United States Patent [19]

Kurtz et al.

[11] Patent Number: 4,943,288
[45] Date of Patent: Jul. 24, 1990

[54] LIQUID REINFUSION BAG SYSTEM

[75] Inventors: Leonard D. Kurtz, Woodmere; Joseph LiCausi, Port Jefferson Station, both of N.Y.

[73] Assignee: BioResearch, Inc., Farmingdale, N.Y.

[21] Appl. No.: 420,718

[22] Filed: Oct. 13, 1989

Related U.S. Application Data

[63] Continuation of Ser. No. 364,583, Jun. 12, 1989, abandoned, which is a continuation of Ser. No. 160,293, Feb. 25, 1988, abandoned.

[51] Int. Cl.$^5$ ............................................. A61M 5/14
[52] U.S. Cl. ................................... 604/408; 604/4; 604/311
[58] Field of Search ............................ 604/406–410, 604/4–6, 259, 362, 319, 317, 318, 320, 262; 248/317, 322–324, 95, 97, 99; 128/767–768, DIG. 24

[56] References Cited

U.S. PATENT DOCUMENTS

| | | | |
|---|---|---|---|
| 1,971,642 | 8/1934 | Champlin | 248/97 |
| 2,470,977 | 5/1949 | Chidsey | 248/97 |
| 2,908,463 | 10/1959 | Chenette | 248/95 |
| 3,211,144 | 10/1965 | Nehring | 128/214 |
| 3,601,119 | 8/1971 | Engelsher | 128/708 |
| 3,650,272 | 3/1972 | Ericson | 604/238 |
| 3,872,868 | 3/1975 | Kline | 128/DIG. 24 |
| 4,086,925 | 5/1978 | Dodge | 128/DIG. 24 |
| 4,126,135 | 11/1978 | Hinman | 604/326 |
| 4,161,179 | 7/1979 | Abramson | 128/DIG. 24 |
| 4,175,602 | 11/1979 | Cavalaris | 248/97 |
| 4,295,619 | 10/1981 | Kulin | 248/95 |
| 4,305,389 | 12/1981 | Potter | 248/95 |
| 4,312,352 | 1/1982 | Meisch et al. | 128/294 |
| 4,326,526 | 4/1982 | Bock et al. | 128/DIG. 24 |
| 4,393,880 | 7/1983 | Taylor | 604/317 |
| 4,443,220 | 11/1984 | Haver | 604/319 |
| 4,449,969 | 5/1984 | Schweizer | 604/322 |
| 4,500,308 | 2/1985 | Kurtz et al. | 604/4 |
| 4,501,581 | 2/1985 | Kurtz et al. | 604/52 |
| 4,501,584 | 2/1985 | Cianci et al. | 604/322 |
| 4,543,084 | 4/1985 | Bailey | 248/97 |
| 4,553,970 | 11/1985 | Lewis | 604/408 |
| 4,637,934 | 1/1987 | White | 605/408 |
| 4,642,088 | 2/1987 | Gunter | 604/4 |
| 4,650,478 | 3/1987 | Dunn | 604/322 |
| 4,664,652 | 5/1987 | Weilbacher | 604/324 |
| 4,700,871 | 12/1987 | Matsuo | 604/408 |
| 4,781,707 | 11/1988 | Boehringer et al. | 604/317 |
| 4,838,872 | 8/1989 | Sherlock | 604/319 |
| 4,857,042 | 8/1989 | Schneider | 604/4 |

FOREIGN PATENT DOCUMENTS

| | | |
|---|---|---|
| 856750 | 12/1968 | United Kingdom . |
| 2189773 | 11/1987 | United Kingdom . |
| 1573437 | 8/1988 | United Kingdom . |

Primary Examiner—Randall L. Green
Assistant Examiner—K. M. Reichle
Attorney, Agent, or Firm—Larson & Taylor

[57] ABSTRACT

A liquid reinfusion bag system is provided for collecting blood from a surgical site and/or reinfusing the collected blood into the patient. The system includes a flexible bag having an external frame with locking elements to retain the bag in extended position during the time the bag is being filled, the locking elements being displaceable to permit the bag to collapse during the reinfusion process.

5 Claims, 2 Drawing Sheets

LIQUID REINFUSION BAG SYSTEM

This application is a continuation of application Ser. No. 364,583 filed Jun. 12, 1989, now abandoned, which is a continuation of application Ser. No. 160,293 filed Feb. 25, 1988, now abandoned.

BACKGROUND OF THE INVENTION

The present invention relates to a liquid reinfusion flexible bag system having an external supporting frame with releasable locking elements so as to permit the bag to be maintained in an opened position while the bag is being filled or permitted to collapse during reinfusion by releasing the frame locking elements.

It is well known in the prior art to provide flexible bags for collecting blood from a surgical site by applying suction to the bag so as to draw the liquid from the surgical site into the bag. Such devices provide means for retaining the bag in an open position during the filling operation and for collapsing the bag during the reinfusion step. Such a device is disclosed in U.S. Pat. No. 4,500,308, issued Feb. 19, 1985.

The prior art also discloses various means for supporting flexible bags externally such as U.S. Pat. Nos. 4,393,880; 4,312,352; 4,650,478 and 4,501,584. Such devices also include frames for maintaining flexible bags in an extended position such as disclosed in U.S. Pat. No. 4,449,969. However, such frames are expensive, difficult to handle and do not provide means for permitting the flexible bag to collapse when it is being emptied.

SUMMARY OF THE INVENTION

According to the present invention, there is provided a flexible bag having frame members integrally formed externally of the bag with crossed locking arms detachably disposed on each end of the bag. When it is desired to maintain the bag in an extended position, the locking arms on each end of the bag are engaged with the frame members so as to hold the bag in its extended condition. During use, when the bag is totally filled with blood drawn from the surgical site, the locking arms are detached from the frame so that as blood is withdrawn from the bag for reinfusion, the bag will collapse to permit free flow of the blood from the bag.

An object of the present invention is to provide a flexible container with means for locking the container in an extended position wherein the locking elements may be removed from the bag to permit the bag to collapse.

Another object of the present invention is to provide a flexible bag with integrally formed frame members disposed at spaced points around the periphery of the container with locking arms disposed at each end of the bag which may be moved between locked position in engagement with the frame members to retain the bag in an extended position to an unlocked position wherein the bag may collapse.

Other objects of the present invention will become more readily apparent upon consideration of the following detailed specification taken in connection with the accompanying drawings wherein:

DETAILED DESCRIPTION OF THE INVENTION

Figure 1:
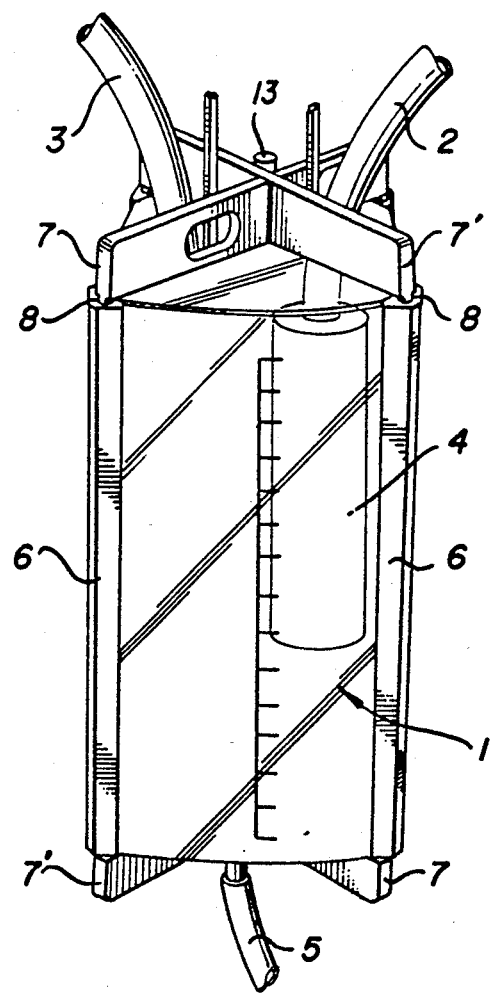
FIG. 1 is a perspective elevational view of a blood bag incorporating the locking means according to the present invention.

Referring now more specifically to the drawings wherein like numerals indicate like parts throughout the several views, there is shown at 1 in FIG. 1 a flexible bag of a generally cylindrical configuration having end walls integrally formed therewith. The bag is provided with an inlet tube 2 which provides a means for withdrawing blood from a surgical site into the bag through a filter 4 on the inner end therof having a 170 micron mesh. A second tube 3 is provided at the upper end of the bag for connection with a suction source. The inner end of the tube 3 is provided with a restrictor (not shown) which has sufficiently small openings therein which only permits air to pass therethrough. The opposite end of the bag is provided with an IV spike or reinfusion tube 5. The bag is also provided with a separate port 13 at the upper end for adding heparin or other substances to the blood within the bag.

Figure 2:
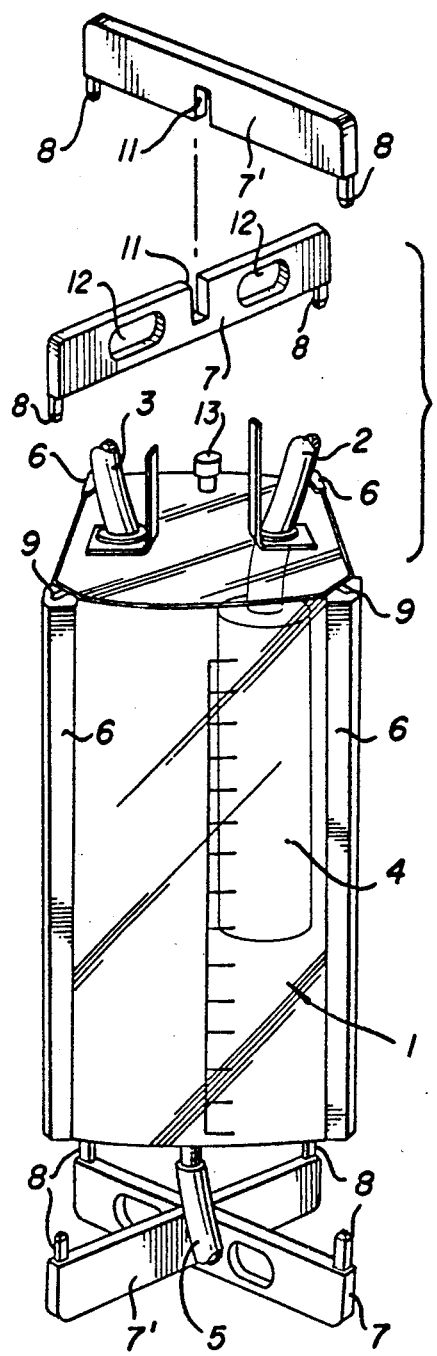
FIG. 2 is a elevational view of the bag when filled with liquid with the locking means disengaged from the bag and in disassembled position.

There is provided means for locking the bag in a fully extended position and this means includes a plurality of spaced frame members 6 which are formed of a relatively rigid material and which may be integrally formed with the bag or alternatively may be secured at each end portion therof to the flexible bag. At each end thereof the frame members 16 are provided with a pair of crossed locking arms 7 and $7^1$. As shown in FIG. 2 the locking arms are connected together by central interengaging slots 11. One of each pair of locking arms 7 and $7^1$ may be provided with finger apertures 12 to facilitate removal of the arms from the bag. These locking arms are provided with pins 8 on the outer ends thereof and these pins engage in openings 9 in the ends of frame members 6. In the specific embodiment shown, there are four frame members 6 spaced 90° apart around the periphery of the flexible bag 1. When the four locking arms 7 and $7^1$ have the pins 8 in engagement within the openings 9 of frame members 6 at both ends of bag 1 as shown in FIG. 1, the flexible bag is maintained in its extended position. By providing separable locking arms the insertion of the arms on the bag is facilitated in that each arm is separately engaged with the bag.

Figure 3:
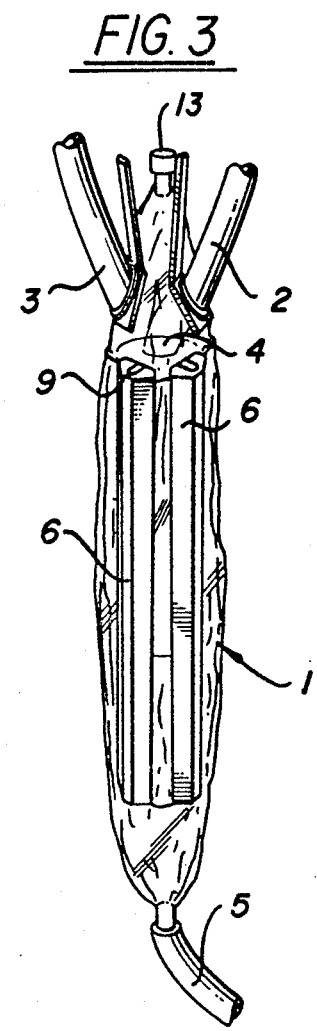
FIG. 3 is a similar view showing the bag being emptied.

When it is desired to permit the bag to collapse, the crossed locking arms 7 and $7^1$ are removed from engagement with the frame members 6 so as to permit the walls of the bag to collapse as shown in FIG. 3.

In use the flexible bag 1 is extended to its open position by moving the locking arms 7 and $7^1$ into engagement with both the upper and bottom walls of the bag with the pins 8 in engagement within the apertures 9. The bag is supported in any convenient manner adjacent to the patient and the outer end of the inlet tube 2 is placed at the surgical site. The tube 5 is closed off and the tube 3 is connected to any suitable source of suction. Blood from the surgical site will then be drawn into the flexible bag 1 which will maintain its extended open position by the frame members 6 and locking elements 7 and $7^1$ serving to prevent collapse of the bag. When the bag is filled the inlet tube 2 is clamped off and the suction tube 3 is removed from the source of suction and clamped off. The locking arms 7 and $7^1$ are then removed from engagement with the frame members 6.

The reinfusion tube 5 is connected with an IV needle passing into the circulatory system of the patient. Blood will then flow from the bag 1 back into the patient through reinfusion tube 5. If necessary, external pressure may be applied to the bag to force the bag towards a collapsed position.

Obviously, many modifications and variations of the present invention are possible in light of the foregoing teachings. What is claimed as new and is desired to be secured by Letters Patent is:

1. A reinfusion bag including a flexible container having a side wall and top and bottom end walls, an inlet tube in the top end wall, an outlet tube adapted to be connected to a suction source in the top end wall, a reinfusion tube in the bottom end wall, a plurality of relatively rigid frame members disposed around and connected to the side wall of the flexible container, and locking means releasably attached to said frame members and extending across the top and bottom end walls for retaining the end walls of the flexible container in an extended position so that the container is maintained in an open position.

2. A reinfusion bag according to claim 1 wherein the locking means includes cross locking arm means on each end of the flexible container for retaining the end walls of the flexible containers in an extended position.

3. A reinfusion bag according to claim 2 and further including pins on said locking arm means and apertures in the frame members whereby said pins engage said apertures to maintain the container in an open position.

4. A reinfusion bag having a continuous bag sidewall structure including first portions thereof formed of flexible material and second portions thereof formed of relatively rigid material, said continuous bag sidewall structure having first and second ends, inlet and outlet ports in said bag, bag endwall structure flexibly enclosing the first and second ends of the sidewall structure whereby the bag may be collapsed with the inner faces of the bag sidewall structure substantially in contact, and rigid means extending across said bag endwall structure releasably engagable with the relatively rigid second portions of said bag for retaining said bag in an extended uncollapsed position so that when said last named rigid means is released and disengaged from said relatively rigid second portions of the bag the bag is readily collapsible.

5. A reinfusion bag according to claim 4 wherein said rigid means is disposed external of said bag.

* * * * *